United States Patent
Knobel et al.

(10) Patent No.: US 11,054,412 B2
(45) Date of Patent: Jul. 6, 2021

(54) MULTI-BED SORBENT TUBES AND USE THEREOF

(71) Applicant: KONINKLIJKE PHILIPS N.V., Eindhoven (NL)

(72) Inventors: Hugo Hubertus Knobel, Eindhoven (NL); Ruud Johannes Theodorus Soers, Budel (NL); Tamara Mathea Elisabeth Nijsen, Weert (NL); Johannes Weda, Nijmegen (NL)

(73) Assignee: Koninklijke Philips N.V., Eindhoven (NL)

( * ) Notice: Subject to any disclaimer, the term of this patent is extended or adjusted under 35 U.S.C. 154(b) by 310 days.

(21) Appl. No.: 15/755,347

(22) PCT Filed: Sep. 9, 2016

(86) PCT No.: PCT/IB2016/055368
§ 371 (c)(1),
(2) Date: Feb. 26, 2018

(87) PCT Pub. No.: WO2017/042716
PCT Pub. Date: Mar. 16, 2017

(65) Prior Publication Data
US 2018/0246078 A1   Aug. 30, 2018

Related U.S. Application Data (60) Provisional application No. 62/217,361, filed on Sep. 11, 2015.

(51) Int. Cl.
*B01D 53/02* (2006.01)
*G01N 33/497* (2006.01)
(Continued)

(52) U.S. Cl.
CPC ....... *G01N 33/497* (2013.01); *G01N 33/0047* (2013.01); *G01N 33/538* (2013.01); *G01N 33/98* (2013.01); *G01N 2033/4975* (2013.01)

(58) Field of Classification Search
CPC ....... G01N 2033/4975; G01N 33/0047; G01N 33/497; G01N 33/538; G01N 33/98
See application file for complete search history.

(56) References Cited

U.S. PATENT DOCUMENTS 4,249,904 A * 2/1981 Rounbehler ........... B01D 53/02
                                                                 436/178
5,522,918 A * 6/1996 Shiramizu ............... G01N 30/12
                                                                 95/87
(Continued)

FOREIGN PATENT DOCUMENTS

CN      101294936 A      10/2008
JP      2007187532 A      7/2007
(Continued)

OTHER PUBLICATIONS

Amaan et al: "The Human Volatilome:Volatile Organic Compounds (VOCs) in Exhaled Breath, Skin Emanations, Urine, Feces and Saliva"; J. Breath Res. 8 (20014) 034001, 17 Page Documente.
(Continued)

*Primary Examiner* — Christopher P Jones
(74) *Attorney, Agent, or Firm* — Daniel H. Brean (57) ABSTRACT

Exhaled breath analysis in health and disease is an area of growing clinical interest with the potential to be adopted through the whole respiratory healthcare continuum. However, currently there is no standard for exhaled breath collection, and the optimal way to preconcentrate the highly humid exhaled breath is not known. Described is an optimized combination of sorbent materials and sample handling methods that allows quantitative capturing of exhaled molecules over a broad range in highly humid conditions.
(Continued)

The invention can be applied in pre-concentration units of future devices for exhaled breath analysis, for example at the bedside.

11 Claims, 4 Drawing Sheets

(51) Int. Cl.
*G01N 33/98* (2006.01)
*G01N 33/538* (2006.01)
*G01N 33/00* (2006.01)

(56) References Cited

U.S. PATENT DOCUMENTS

| | | | |
|---|---|---|---|
| 6,929,672 B1* | 8/2005 | Wakayama | B01D 39/163 55/385.2 |
| 2005/0065446 A1* | 3/2005 | Talton | G01N 33/497 600/529 |
| 2015/0123670 A1 | 5/2015 | Antle et al. | |
| 2017/0303822 A1* | 10/2017 | Allsworth | B01D 46/0028 |
| 2017/0303823 A1* | 10/2017 | Allsworth | A61B 5/6803 |

FOREIGN PATENT DOCUMENTS

| | | |
|---|---|---|
| RU | 2473905 C1 | 1/2013 |
| WO | 2001040793 A1 | 6/2001 |
| WO | 2008025365 A1 | 3/2008 |

OTHER PUBLICATIONS

Buszewski et al: "Human Exhaled Air Analytics: Biomarkers of Diseases"; Biomedical Chromatography, vol. 21, 2007, pp. 553-566.
Hakim et al: "Volative Organic Compounds of Lung Cancer and Possible Biochemical Pathways"; Chemical Review,2012M vol. 12, pp. 5949-5966.
Hayes et al: "Evaluation of Sorbent Methodology for Petroleum-Impacted Site Investigations"; A&WMA "Vapor Intrusion: Learning From the Challenges", Sep. 2007, Providence, RI, 10 Page Document.
Turner et al: "The Effect of a Paced Audditory Serial Addition Test (PASAT) Intervention on the Profile of Volatile Organic Compounds in Human Breath: A Pilot Study"; J. Breath Res. 7 (2013) 017102, 11 Page Document.
Vink et al: "Optimization of Human Breath Sampling for VOC Analysis"; Conference Paper, IABR Summit 2015, Vienna, pp. 1-3.
Woolfenden: "Sorbent-Based Sampling Methods for Volatile and Semi-Volatile Organic Compounds in Air: Part 1: Sorbent-Based Air Monitoring Options"; Journal of Chromatography A, 1217 (2010), pp. 2674-2684.
Performances of the Radiello diffusive sampler for BTEX measurements: Influence of environmental conditions and determination of modelled sampling rates//Atmospheric Environment, 2009, V39, pp. 2535-2544.
Compendium of Methods for the Determination of Toxic Organic Compounds in Ambient Air. Second Edition. Determination of Volatile Organic Compounds in Ambient Air Using Active Sampling Onto Sorbent Tubes. Center for Environment Research Information, OH. Jan. 1999.

* cited by examiner

FIGURE 1

PRIOR ART

FIGURE 2

PRIOR ART

MULTI-BED SORBENT TUBES AND USE THEREOF

CROSS-REFERENCE TO PRIOR APPLICATIONS

This application is the U.S. National Phase application under 35 U.S.C. § 371 of International Application No. PCT/IB2016/055368, filed on Sep. 9, 2016, which claims the benefit of U.S. Provisional Patent Application No. 62/217,361, filed on Sep. 11, 2015. These applications are hereby incorporated by reference herein.

This application claims priority from U.S. Provisional Patent Application No. 62/217,361 having a filing date of Sep. 11, 2015.

BACKGROUND

Exhaled breath analysis in health and disease is an area of growing clinical interest. Using breath as a biological sample may be appealing because breath-collection is cheap, easy to perform and is non-invasive in nature. It has the potential to be adopted throughout the healthcare continuum with an application range varying from the hospital to the home.

As exemplified by the article Biomed Chromatogr. 2007 June; 21(6):553-66, Human exhaled air analytics: biomarkers of diseases, by Buszewski B, Kesy M, Ligor T, Amann A, the prior art literature teaches that many different volatile organic compounds (VOCs) in breath have been associated with diseases. The particular VOCs that are associated with disease range from very volatile molecules with low "C" numbers, such as ethane, acetone, acetaldehyde, to very heavy molecules, such as octadecane. Two exemplary articles describe these associations: 1. Chem. Rev. 2012, 112, 5949-5966, Volatile Organic Compounds of Lung Cancer and Possible Biochemical Pathways, Hakim, M. et al.; and 2. J Breath Res. 2014 September; 8 (3):034001. The human volatilome: volatile organic compounds (VOCs) in exhaled breath, skin emanations, urine, faeces and saliva. Amann A, Costello Bde L, Miekisch W, Schubert J, Buszewski B, Pleil J, Ratcliffe N, Risby T.

A commonly used method to trap VOCs from collected breath is the use of sorbent-containing adsorption tubes. Examples of sorbents include glass beads and substances under the trade names Carbosieve, Carboxen™, Carbotrap™, Tenax™ TA, Tenax™ GR, and Carbograph. Tenax™ for example is a registered trademark of Buchem BV located in Apeldoorn, The Netherlands. Carboxen™ and Carbotrap™ for example are registered trademarks of Sigma-Aldrich Co., St. Louis Mo. Due to the distinct properties of these materials, the sorbent-compound interaction stability and their affinity for water varies.

Figure 1:
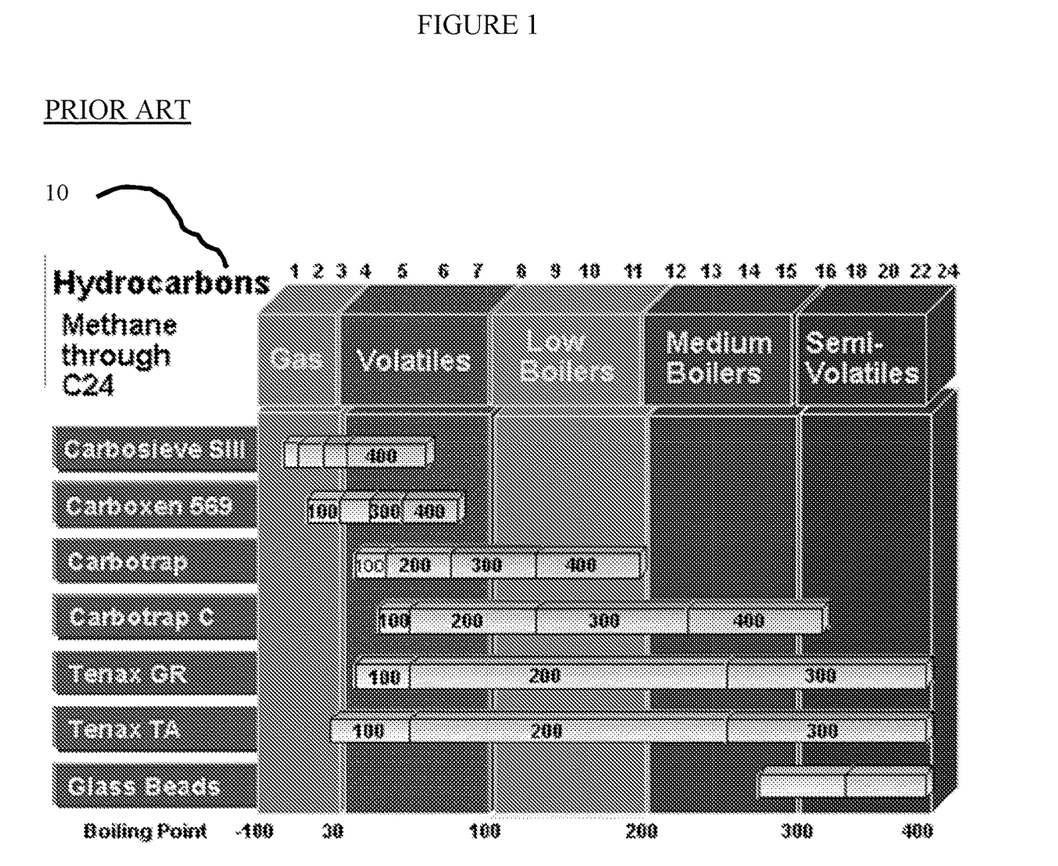
FIG. 1 illustrates an example set of useful sorbents, arranged by their applicability to various hydrocarbons.

FIG. 1 illustrates a graph 10 of several usable sorbent/compound combinations. Carbosieve SIII is a large surface area carbon molecular sieve which is ideal for trapping the smallest organics, the count of carbon atoms in the organic being represented on the x-axis as from C1 (methane) to C24 (tetracosane). While it has a higher affinity for water than most other resins, its small pore size provides the best trapping ability for the volatile organics.

Tenax® TA is a porous polymer resin based on 2.6-diphenylene oxide. It has been specifically designed for the trapping of volatiles and semi-volatiles from air or which have been purged from liquid or solid sample matrices. Both the EPA and NIOSH specify the use of Tenax in their standard methods. Tenax TA is a low bleeding material with a low level of impurities and has replaced Tenax-GC, which was distributed in the past. Tenax TA can be applied both as a column packing material and for traps for organic volatile and semi-volatile compounds. Using thermal desorption techniques such as the S.I.S. Purge and Trap system in conjunction with the Short Path Thermal Desorption System, detection of volatile organics in the ppb and ppt level is feasible. Due to its low affinity for water, Tenax TA is especially useful for the purging and trapping of volatiles from high moisture content samples including the analysis of volatile organic compounds in water. Tenax TA is a specially processed Tenax which is designed primarily as a trapping agent, and has very low levels of impurities.

The Tenax® GR compound is a composite material of Tenax® TA and 30% graphite. The resulting material gives a higher breakthrough volume for most volatile organics, yet still has a low affinity for water. In addition, Tenax GR maintains its high temperature stability to 350 degrees C. These properties make Tenax GR an ideal adsorbent for the trapping of volatiles from air, water and solid samples. Using thermal desorption techniques such as the S.I.S. Purge and Trap system in conjunction with the Short Path Thermal Desorption System, detection of volatile organics in the ppb and ppt level is feasible.

Tenax™ GR is especially useful for the purging of volatiles from high moisture content samples including the analysis of volatile organic compounds in water. Since its density is twice that of Tenax TA, this enables a larger amount of the Tenax GR resin to be placed inside the desorption tube, thereby increasing the ability to retain volatiles on a small resin bed.

Due to their low affinity for water, Carbotrap and Carbotrap C are graphitized carbon blacks that are ideal adsorbent resins for the trapping of a wide range of organic analytes from C4/C5 through the medium boilers. They have a coarse mesh size (20/40) which prevent high backpressures in desorption tubes.

Carboxen™ comprises a carbon molecular sieve (CMS) which is the porous carbon skeletal framework that remains after pyrolysis of a polymeric precursor. These particles are spherical (better packed bed performance than granular particles), hard and non-friable (pack well, will not break), highly porous (high surface areas), used for molecules with an analyte size relative to C2-C5 n-alkanes, and are hydrophobic so can be used in high humidity environments. Generally, CMS adsorbents offer greater relative adsorptive strength compared to spherical graphitized polymer carbon (SGPC) and graphitized carbon black (GCB) adsorbents. Carboxen adsorbents have tapered pores, resulting in excellent thermodynamic properties for both adsorption and desorption (have the best thermodynamic performance of any adsorbents). Their surface chemistry can be tailored for specific target analytes.

Carbotrap® adsorbents are a graphitized carbon black (GCB) that can be non-porous or porous. The graphitization process results in a highly pure surface with great adsorption and desorption (if required) properties. Surface interactions depend solely on dispersion (London) forces. These particles are granular, friable, and are used for molecules with an analyte size relative to C3-C20+n-alkanes. They are hydrophobic so can be used in high humidity environments. Generally, GCB adsorbents offer weaker relative adsorptive strength compared to carbon molecular sieve (CMS) adsorbents, and similar relative adsorptive strength compared to spherical graphitized polymer carbon (SGPC) adsorbents.

Carbotrap adsorbents particles are 20/40 mesh. These large particles allow high flow rates without excessive pressure drops.

Carbograph™ packings are graphitized carbon blacks equivalent to Carbopack packings. There are three different types of graphitized carbon blacks, Carbograph™ 1 2 and 5. Unlike diatomites that must have a stationary phase, Carbograph™ packings possess partitioning properties without any surface modifications.

Carbograph™ packings can also be modified with a stationary phase giving them unique selectivities. Carbograph™ 1 is equivalent to Carbopack™ B, and is obtained by graphitization and granulation. It has a surface area of 100 m2/g. Carbograph™ 1-TD (also referred to as Carbograph 1TD) has a coarse mesh of 20/40 which is suitable for thermal desorption work. Maximum temperature is 500 degrees C. Carbograph™ 1SC is similar to Carbopack™ BHT. It is a type of Carbograph™ 1 that is manufactured specifically for the separation of sulfur compounds SF6, SO2, H2S, COS, mercaptans, and disulfides. It is also suitable for analysis of sulfurs in oil products. Maximum temperature is 225 degrees C. Carbograph™ 2 is equivalent to Carbopack™ C. It has a specific surface of 10 m2/g. It can be used alone as an uncoated adsorbent packing for the separation of volatile organic compounds. Carbograph™ 2-TD has a coarse mesh of 20/40 which is suitable for thermal desorption work. Maximum temperature is 500 degrees C. Carbograph™ 5TD is a medium-to-strong strength sorbent which has a specific surface area of about 560 square meters per gram, which is about 5 times that of Carbograph 1TD. Carbograph™ 5TD has an approximate analyte volatility range of n-C3/4 to n-C8 with a boiling point of 50° C. to 150° C. Example analytes for Carbograph 5TD are light hydrocarbons. Both Carbograph 1TD and 5TD are hydrophobic.

Several problems still exist in the prior art, however. For example, the practice of capturing and analyzing breath samples is still in its infancy and so presently there is no standardized method available to capture and store breath.

Usually rather arbitrary choices are made in combining sorbent materials and sample volumes. Complications due to the high humidity of exhaled breath, mismatched sample volumes and the wrong choice of sorbent materials prevent quantitative capturing of exhaled molecules. Thus, the erroneous capturing also may lead to erroneous inferences from the data.

Figure 2:
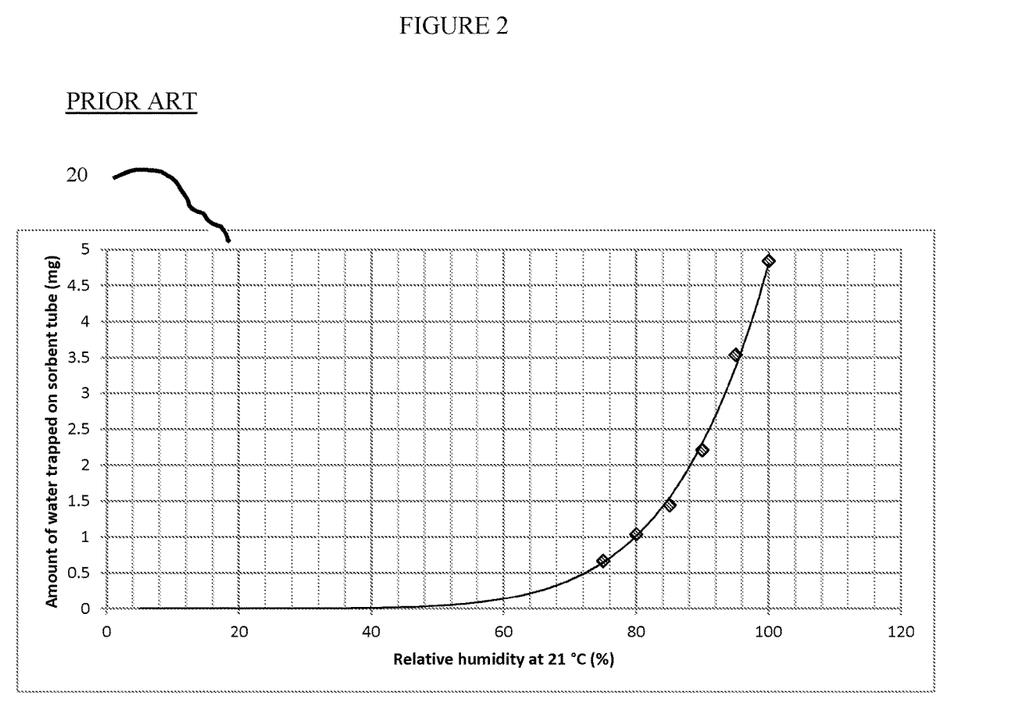
FIG. 2 illustrates the trapping of water in an absorbent tube as a function of relative humidity.

The need for proper water management is illustrated in FIG. 2, which shows in a graph 20 the amount of water that can be absorbed on a sorbent tube at different relative humidity (RH). At 100% RH at 21° C., 5 mg of water is absorbed, which is a factor of $>10^6$ than most compounds of interest present in breath parts-per-billion Volatiles (ppbV). The competition between water and VOCs for the active sites of the sorbent makes trapping of VOCs less efficient. This reduced efficiency causes loss of molecules of interest, i.e. breakthrough, and poor reproducibility.

Secondly, the high water content in a sample is detrimental to the chromatographic process. For example, high water content causes problems during injection, the loss of separation and rapid column deterioration.

The prior art needs solutions to the limitations posed by the use of humidity/moisture traps which can irreversibly trap small and/or polar/water soluble VOCs. This invention overcomes those limitations through a novel and non-obvious selection of combinations of sorbent tube materials in a proper sequence and proportion.

SUMMARY OF THE INVENTION

While combining different sorbents into one sorbent sampling tube is known, the inventors have discovered an optimal combination of sorbents, their arrangement within the tube, and their proportions. In addition, the inventors have discovered an optimal drying gas volume needed to remove captured moisture from the tubes while retaining VOCs of interest in the tube for later analysis.

In accordance with the principles of the invention, a multi-bed sampling tube combined with a sampling method is described which is capable of quantitatively trapping and releasing VOCs, wherein the VOCs of interest range from compounds having a boiling point between that of butane (C4) to pentadecane (C15). The organic compounds can be trapped from a high humidity (0-100% RH gas flow/environment such as that found in exhaled breath without the chromatographic and trapping issues due to the presence of excess water. After trapping the sample, the tube is dried using an extremely clean gas (e.g. helium, nitrogen) to remove excess water. The method can remove ≥99% of the humidity present in the tube sample. The tube/method combination enables trapping and release of the organic compounds present in sub-parts per billion (ppb) levels.

The inventors note that maximum sampling volumes are linearly related to the amount of sorbent. For example, doubling the amount doubles the maximum sampling volume and also doubles the drying time. Increasing the amount of sorbent and sampling volume decreases the limit of detection of the method.

After the method for drying of the multi-bed sampling tube, the tube can be stored (e.g. in a refrigerator) for at least one month without loss of VOCs.

Figure 3:
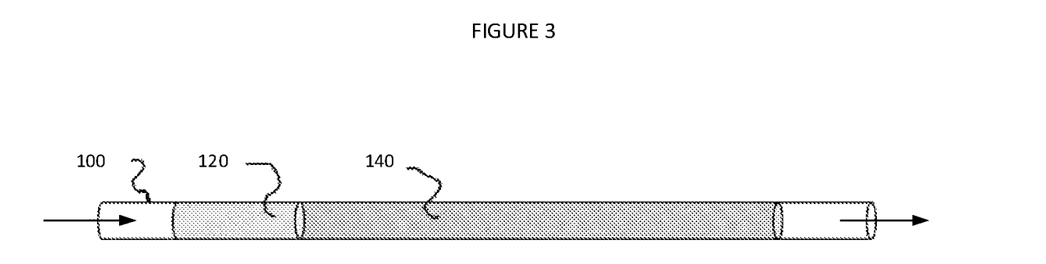
FIG. 3 illustrates a first embodiment of an inventive absorbent tube, having an optimized arrangement of two different absorbents and their relative quantities.

In accordance with the above principles, multi-bed sorbent tube comprises a sampling tube 100 arranged to guide a flow of gas from an one end to a second end. The sampling tube 100 contains a first volume 120 of a substance disposed within the tube near the one end and having a chemical composition substantially like Tenax GR and a second volume 140 of a substance disposed within the tube and between the first volume and the second end and having a chemical composition substantially like Carbograph 5TD. The proportions of the first volume and the second volume are about 21.5% and 78.5% respectively.

In another embodiment, the aforedescribed multi-bed sorbent tube has an amount of the first volume of about 85 milligrams, and an amount of the second volume of about 300 milligrams.

Figure 4:
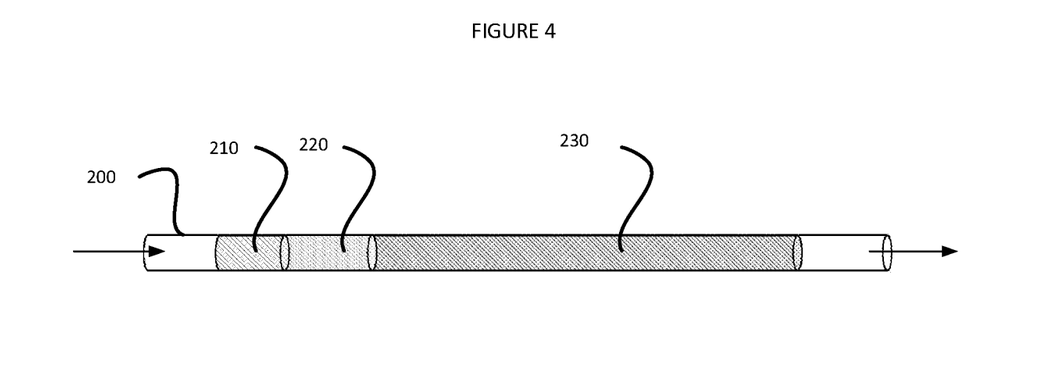
FIG. 4 illustrates a second embodiment of an inventive absorbent tube, having an optimized arrangement of three different absorbents and their relative quantities.

In an alternative embodiment of the invention, a multi-bed sorbent tube is described, comprising a sampling tube 200 arranged to guide a flow of gas from an one end to a second end. The sampling tube 200 contains a first volume 210 of a substance disposed within the tube near the one end and having a chemical composition substantially like Tenax TA and a second volume 220 of a substance disposed within the tube and between the first volume and the second end and having a chemical composition substantially like Carbograph 1TD and a third volume 230 of a substance disposed within the tube and between the second volume and the second end and having a chemical composition substantially like Carbograph 5TD. The proportions of the first volume, the second volume, and the third volume are about 12.1%, 16.5% and 71.4% respectively.

In another embodiment of the invention, a method for analyzing the VOC content of a humid gas from a source comprises the steps of providing a multi-bed sorbent tube comprising two or more compounds, each compound having a chemical composition substantially like Tenax GR, Carbograph 5TD, Tenax TA, Carbograph 1TD, or Carbograph 5TD. The method then proceeds by the step of first passing a first volume of a humid gas containing water and one or more volatile organic compounds (VOCs) through the multi-bed sorbent tube, whereby the VOCs and the water are retained in the sorbent tube, and then a second passing a second volume of dry gas through the multi-bed sorbent tube for a period of time sufficient to remove an amount of the water retained by the sorbent tube during the first passing step. The method further describes the steps of desorbing the multi-bed sorbent tube to remove the VOCs retained by the sorbent tube during the first passing step and analyzing the removed VOCs to determine the VOC quantity and identity.

An embodiment of the afore described method includes wherein the source is selected from one of the group consisting of a medical ventilator exhalation tube side stream, a collection bag, an air volume in an incubator, an air volume in a high humidity room, and an exhaust from an internal combustion engine. The first volume may be about 1.2 liters. The second volume may be selected to be sufficient to remove about 99 percent of the water retained by the sorbent tube.

Another embodiment of the method describes wherein one of the two or more compounds is about 85 milligrams of a chemical composition substantially like Tenax GR and a second one of the two or more compounds is about 300 milligrams of a chemical composition substantially like Carbograph 5TD, and further wherein the first volume is about 1.2 liters, and further wherein the second volume is about 100 standard cubic centimeters for a duration of about 7 minutes.

In another embodiment of the method, the one of the two or more compounds is about 12.1 percent by volume of a chemical composition substantially like Tenax TA, a second one of the two or more compounds is about 16.5 percent by volume of a chemical composition substantially like Carbograph 1TD, and a third one of the two or more compounds is about 71.4% by volume of a chemical composition substantially like Carbograph 5TD, and further wherein the first volume is about 1.2 liters, and further wherein the second volume is about 100 standard cubic centimeters per minute for a duration of about 6.5 minutes. With these combinations of materials, an optimal desorbing step may include heating the sorbent tube to about 225 degrees Celsius for about 4 minutes.

The method may also include a step of storing the sorbent tube between the second passing step and the desorbing step for a maximum storage time of about two months. The analyzing step of the above described method may include the VOC identity as one or more of organic molecules ranging from C4 to C15. The first volume may be linearly related in size to an amount of the two or more compounds. The second volume may be linearly related in size to an amount of the two or more compounds.

In another embodiment, the afore described method may be substantially automated, wherein one or both of the first passing step and the second passing step are conducted automatically by a sampling device under the control of a software program residing on non-volatile computer memory.

DETAILED DESCRIPTION OF THE EMBODIMENTS

The sampling tubes of the present invention are comprised of various combinations and proportions of sorbents enabling trapping of organic compounds ranging from at least C4 to C15. The multi-bed adsorption tubes are constructed in such a way that, after sampling, the adsorbent can be sufficiently dried using extremely clean gas (such as nitrogen, helium, and air) without the loss of any of the organic compounds to be measured, removing ≥99% of the humidity present on the tube.

Desorption of the tubes should be undertaken at temperatures as low as possible to minimize thermal degradation of sampled organic compounds and the adsorption bed itself, reducing loss of analytes and introduction of unwanted organic compounds.

The inventors have discovered that the following particular combinations and proportions of trapping materials in sorbent tubes optimally fulfill the objectives of the present invention. In particular, these combinations and proportions are suitable for capturing humid exhaled breath samples from animals including humans.

Embodiment 1

Now turning to FIG. 3, for quantitatively trapping of a large range of volatiles varying from at least C4 to C15 from a 100% RH gas stream, disclosed the following optimal composition of a multi-bed sorbent tube:

A sampling tube 100 is arranged to capture samples from a flowing gas that enters at one end, as indicated by the left arrow in FIG. 3, and that exits at a second end as shown by the right arrow in FIG. 3. The sampling tube itself is disposed such as to be filled with a first volume of a substance substantially like Tenax GR (21.5 vol %) 120 and a second volume of a substance substantially like Carbograph 5TD (78.5 vol %) 140. As shown, The Tenax GR material is disposed closer to the inlet, i.e. upstream, of the sorbent tube than the Carbograph 5TD material. The Carbograph 5TD material is thus disposed downstream of the Tenax GR material and closer to the second end. The proportions of the first volume and the second volume are, as indicated, about 21.5% and 78.5% by volume respectively.

Using this adsorption tube, sampling volumes are limited by the volume of the adsorption bed. An example of how the sample volume relates to the volume of the sorbent bed follows:

If the sorbent tube sampling bed is filled with 85 milligrams of Tenax GR and 300 milligrams of Carbograph 5TD, an optimal sample volume is 1.2 liters (L). After sampling, the tubes must be dried using a 100 standard cubic centimeters per minute (sccm) flow of dry, extremely clean gas. The drying time is also determined by the adsorption bed size. In this embodiment, the tubes are dried for 7 minutes. After sampling and drying, desorption is performed at 225° C. for 4 minutes (also based on the size of this adsorption bed).

When a stream of highly humid gas (for example of human breath) is sampled, this combination can quantitatively trap and release C4-C15 organics that may be useful in later diagnosing of human disease.

Embodiment 2

Now turning to FIG. 4, for quantitatively trapping of a large range of volatiles varying from at least C4 to C15 from a 100% RH gas stream, disclosed is the following optimal composition of a multi-bed sorbent tube:

A sampling tube 200 is arranged to capture samples from a flowing gas that enters at one end, as indicated by the left arrow in FIG. 4, and that exits at a second end as shown by the right arrow in FIG. 4. The sampling tube 200 itself is disposed such as to be filled with, arranged respectively from upstream inlet to downstream outlet, a first volume of a substance substantially like Tenax TA (12.1 vol %) 210, a second volume of a substance substantially like Carbograph 1TD (16.5 vol %) 220 and a third volume of a substance substantially like Carbograph 5TD (71.4 vol %) 230. As illustrated, the first volume 210 is disposed within the sorbent tube 200 nearest the one inlet end, the second volume 220 is disposed within the sorbent tube 200 between the first volume and the second outlet end, and the third volume 230 is disposed within the sorbent tube 200 between the second volume 220 and the second outlet end. The proportions of the first, second, and third volumes are, as indicated, about 12.1%, 16.5% and 71.4% by volume respectively.

Using this exemplary adsorption tube 200, sampling volumes are limited by the volume of the adsorption bed. After sampling, the tube 200 may be dried using a 100 sccm flow of dry, extremely clean gas. The optimal drying time is determined by the adsorption bed size, so that in this case the tube 200 is dried for 6.5 minutes.

After sampling and drying, desorption is performed at 225° C. for 4 minutes (based on the size of this adsorption bed).

When a stream of highly humid gas (for example of human breath) is sampled, this combination can quantitative trap and release C4 through C15 organics that may be useful in later diagnosing of human disease.

These recited combinations of sorbents and sample volume are specifically optimized for capturing a broad range of volatile organic compounds in high humidity gas flows/environments. One example of an application would be exhaled breath analysis. Breath sampling can be done via a side stream in a mechanically ventilated patient (intensive care, patient monitoring, home monitoring), patient breathing in a collection bag where the sample is collected from (patient monitoring, home monitoring).

Another example of an application area is neonatal monitoring where the breath from a neonate can be monitored directly or the air in an incubator is monitored (neonatal monitoring).

Other pre-concentration of organic compounds present in high humidity environments such as indoor air, greenhouses and the ambient air in humid climates, or from sampling from internal combustion engine exhausts may be useful with the inventive sorbent tubes 100/200.

Figure 5:
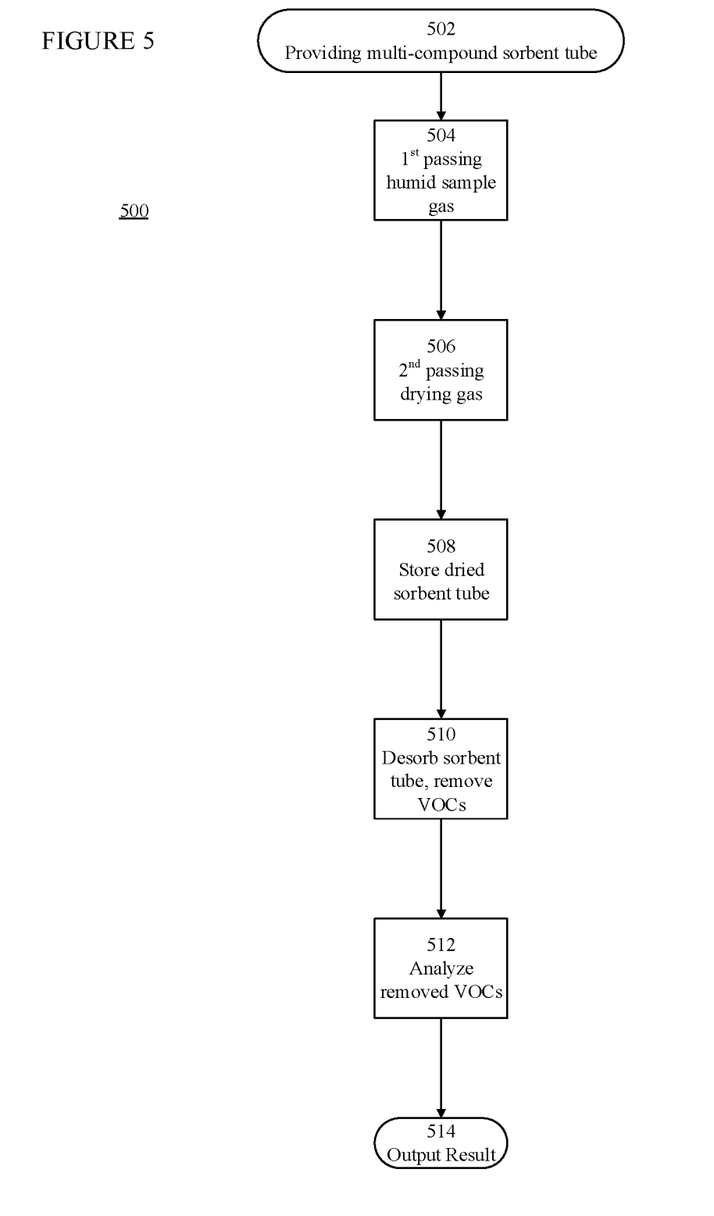
FIG. 5 illustrates a method flow chart for a method for capturing, drying, storing, and analyzing a humid gas sample.

With reference to FIG. 5, a method 500 for analyzing the VOC content of a humid gas from a source is described. The source is preferably from a source of exhaled gas received from a medical ventilation device, such as from a medical ventilator exhalation tube side stream, a collection bag, an air volume in an incubator, or from an air volume in a high humidity room, but could alternatively be for non-medical purposes such as from the exhaust from an internal combustion engine.

The method 500 begins at the providing step 502, which comprises the providing of a multi-bed sorbent tube comprising two or more compounds. Each compound has a chemical composition substantially like Tenax GR, Carbograph 5TD, Tenax TA, or Carbograph 1TD. Examples of sorbent tubes in this providing step are previously described in Embodiment 1 and Embodiment 2, but may be other similar combinations and proportions of compounds.

The method proceeds at a step 504 of first passing a first volume of a humid gas containing water and one or more volatile organic compounds (VOCs) through the multi-bed sorbent tube, whereby the VOCs and the water are retained in the sorbent tube. The sample gas volume, as previously described, should be controlled such that an optimal volume for the amount and type of compounds residing within the sorbent tube. For example, the first volume may be linearly related in size to an amount of the two or more compounds. A previous example volume is 1.2 L for the combination of Embodiment 1. At the conclusion of this first passing step 504, the sorbent tube compositions will hold a sample of water and VOCs, the VOCs in proportion to the VOCs in the first volume.

The sample is then dried via a drying step 506. The step 506 of a second passing a second volume of dry gas through the multi-bed sorbent tube for a period of time sufficient to remove an amount of the water retained by the sorbent tube during the first passing step. Preferably, the second volume is sufficient to remove about 99 percent of the water retained by the sorbent tube. The second volume could be predetermined based on the expected type of sample and the particular sorbent tube compounds used, or could be dynamically determined based on the humidity of the dry gas after passing through the sorbent tube. In one embodiment, this second volume is linearly related in size to an amount of the two or more compounds residing within the sorbent tube. In a method using the sorbent tube of Embodiment 1, the second volume is preferably about 100 standard cubic centimeters per minute for a duration of about 7 minutes. In a method using the sorbent tube of Embodiment 2, the second volume is preferably about 100 standard cubic centimeters per minute for a duration of about 6.5 minutes.

Once the sample is dried at step 506, it may be optionally stored for later analysis. Such storage is often beneficial for reasons of cost-effectiveness (performing multiple analyses at one location and at one time, diagnostic trending and the like. Thus, at storage step 508, the sorbent tube containing the dried VOC sample may be placed in storage, preferably refrigerated storage. The inventors have discovered that the sample retains its accuracy up to a maximum storage time of about two months.

After the sample is dried, and alternatively after the sample has been stored for a desired time in step 508, the sample is retrieved for further processing. The next step in the inventive method is the desorbing step 510. Step 510 comprises desorbing the multi-bed sorbent tube to remove the VOCs retained by the sorbent tube during the first passing step. In a preferred embodiment, the desorbing step 510 further comprises heating the sorbent tube to about 225 degrees Celsius for about 4 minutes to release the retained VOCs. The desorbed VOCs are then available for analysis.

The method further comprises the analyzing step 512 of analyzing the removed desorbed VOCs to determine the VOC quantity and identity. Analyzing step 512 is suitable for identifying and quantifying the VOC identity as one or more of organic molecules ranging from C4 to C15. Information regarding the VOC identity and quantity may then be passed to an output step 514, which is preferably a visual or computer record display of the information that is easily understood by the method user.

The afore-described methods may be conducted by hand, or may be substantially automated. In particular, one or both of the first passing step 504 and the second passing step 506 may be conducted automatically by an automated sampling device under the control of a software program residing on non-volatile computer memory.

Additional modifications to the device, method, and displays as described above are encompassed within the scope of the invention. For example, the selection of particular sorbent tube compositions may differ somewhat from the precise descriptions of the materials. In particular, compositions may differ as to minor ingredients which do not affect the claimed benefits of the claimed mixtures. Methods may differ within the scope of the invention somewhat, depending on for example the amount of material in each sorbent tube.

The invention claimed is:

1. A method for analyzing the volatile organic compound content of a humid gas from a medical ventilator exhalation tube side stream, the method comprising the steps of:
   providing a multi-bed sorbent tube comprising two or more compounds, each compound being a composite material of a porous polymer resin based on 2.6-diphenylene oxide and 30% graphite, a graphitized carbon blacks having a specific surface area of about 560 square meters per gram, a porous polymer resin based on 2.6-diphenylene oxide, or a graphitized carbon blacks having a coarse mesh of 20/40;
   first passing a first volume of the medical ventilator exhalation tube side stream containing water and one or more volatile organic compounds through the multi-bed sorbent tube, whereby the volatile organic compounds and the water are retained in the sorbent tube;
   second passing a second volume of dry gas through the multi-bed sorbent tube for a period of time sufficient to remove an amount of the water retained by the sorbent tube during the first passing step;
   desorbing the multi-bed sorbent tube to remove the volatile organic compounds retained by the sorbent tube during the first passing step; and
   analyzing the removed volatile organic compounds to determine the volatile organic compounds quantity and identity.

2. The method of claim 1, wherein the first volume is 1.2 liters.

3. The method of claim 1, wherein the second volume is sufficient to remove 99 percent of the water retained by the sorbent tube.

4. The method of claim 1, wherein one of the two or more compounds is 85 milligrams of the composite material of a porous polymer resin based on 2.6-diphenylene oxide and 30% graphite and a second one of the two or more compounds is 300 milligrams of the graphitized carbon blacks having a specific surface area of about 560 square meters per gram, and further wherein the first volume is 1.2 liters, and further wherein the second volume is 100 standard cubic centimeters per minute for a duration of 7 minutes.

5. The method of claim 1, wherein one of the two or more compounds is 12.1 percent by volume of the porous polymer resin based on 2.6-diphenylene oxide, a second one of the two or more compounds is 16.5 percent by volume of the graphitized carbon blacks having a coarse mesh of 20/40, and a third one of the two or more compounds is 71.4% by volume of the graphitized carbon blacks having a specific surface area of about 560 square meters per gram, and further wherein the first volume is 1.2 liters, and further wherein the second volume is 100 standard cubic centimeters per minute for a duration of 6.5 minutes.

6. The method of claim 4, wherein the desorbing step further comprises heating the sorbent tube to 225 degrees Celsius for 4 minutes.

7. The method of claim 1, further comprising the step of storing the sorbent tube between the second passing step and the desorbing step for a maximum storage time of two months.

8. The method of claim 1, wherein the analyzing step volatile organic compound identity is one or more of organic molecules ranging from C4 to C15.

9. The method of claim 1, wherein the first volume is linearly related in size to an amount of the two or more compounds.

10. The method of claim 1, wherein the second volume is linearly related in size to an amount of the two or more compounds.

11. The method of claim 1, wherein the first passing step and the second passing step are conducted automatically by a sampling device under the control of a software program residing on non-volatile computer memory.

* * * * *